United States Patent
Benje et al.

(10) Patent No.: US 7,309,471 B2
(45) Date of Patent: Dec. 18, 2007

(54) METHOD FOR PRODUCING UNSATURATED HALOGENIC HYDROCARBONS AND DEVICE SUITABLE FOR USE WITH SAID METHOD

(75) Inventors: Michael Benje, Darmstadt (DE); Horst Ertl, Pleiskirchen (DE); Ingolf Mielke, Burgkirchen (DE); Thomas Wild, Kastl (DE); Peter Kammerhofer, Burgkirchen (DE); Peter Schwarzmaier, Kastl (DE)

(73) Assignee: Uhde GmbH (DE)

(*) Notice: Subject to any disclaimer, the term of this patent is extended or adjusted under 35 U.S.C. 154(b) by 219 days.

(21) Appl. No.: 10/512,880

(22) PCT Filed: Apr. 30, 2003

(86) PCT No.: PCT/EP03/04519

§ 371 (c)(1), (2), (4) Date: Jan. 11, 2005

(87) PCT Pub. No.: WO03/093207

PCT Pub. Date: Nov. 13, 2003

(65) Prior Publication Data

US 2005/0124835 A1 Jun. 9, 2005

(30) Foreign Application Priority Data

May 2, 2002 (DE) ................ 102 19 723

(51) Int. Cl.
  *B01J 19/08* (2006.01)
(52) U.S. Cl. .................... 422/186.1; 422/186.21; 422/187; 570/220
(58) Field of Classification Search ........... 570/220; 422/186.21, 186.1, 187
See application file for complete search history.

(56) References Cited

U.S. PATENT DOCUMENTS

| | | | |
|---|---|---|---|
| 3,051,639 A | 8/1962 | Anderson et al. |
| 3,860,595 A | 1/1975 | Kurtz et al. |
| 3,969,204 A | 7/1976 | Neimann et al. |
| 4,417,964 A | 11/1983 | Wolfrum et al. |
| 4,584,420 A | 4/1986 | Wiedrich et al. |

(Continued)

FOREIGN PATENT DOCUMENTS

DE    1 952 770    5/1971

(Continued)

OTHER PUBLICATIONS

Clark, J.B. et al., "Laser initiated free-radical reactions", Applications of Lasers to Industrial Chemistry 458:82-88 (1984).

(Continued)

*Primary Examiner*—N. Bhat
(74) *Attorney, Agent, or Firm*—Connolly Bove Lodge & Hutz LLP

(57) ABSTRACT

An apparatus for producing ethylenically unsaturated aliphatic halogenic hydrocarbons by thermal cleavage of saturated aliphatic halogenic carbons using an apparatus that introduces an educt gas stream into a reactor which includes at least one supply conduit which opens into the reactor, the supply conduit feeds a heated gas formed from cleavage promotors and radicals produced by a nonthermal plasma device which permits an increased in the yield of the cleavage reaction.

46 Claims, 9 Drawing Sheets

U.S. PATENT DOCUMENTS

Figure 1:
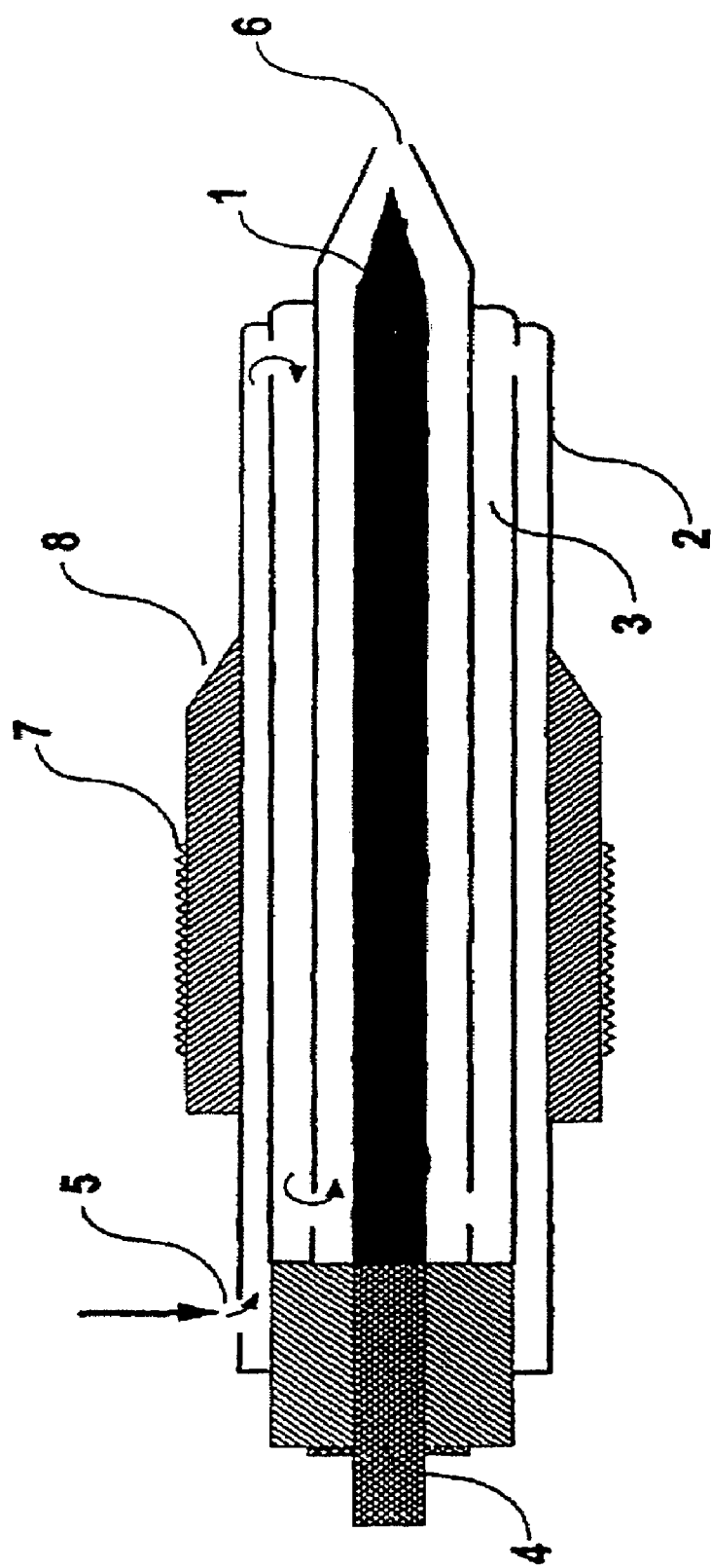

| | | | |
|---|---|---|---|
| 4,590,318 A | 5/1986 | Longhini | |
| 4,595,579 A | 6/1986 | Prudhon et al. | |
| 4,798,914 A | 1/1989 | Link et al. | |
| 4,843,182 A | 6/1989 | Simonetta et al. | |
| 4,851,597 A | 7/1989 | Felix et al. | |
| 5,488,190 A | 1/1996 | Le Blevec et al. | |
| 5,507,920 A | 4/1996 | Schwarzmaier et al. | |
| 5,750,823 A * | 5/1998 | Wofford et al. | 588/316 |
| 5,997,835 A | 12/1999 | Hyldtoft et al. | |
| 6,030,506 A | 2/2000 | Bittenson et al. | |
| 6,166,277 A | 12/2000 | Seidelbach | |
| 6,391,146 B1 * | 5/2002 | Bhatnagar et al. | 156/345.29 |
| 2005/0124835 A1 | 6/2005 | Benje et al. | |

FOREIGN PATENT DOCUMENTS

| | | |
|---|---|---|
| DE | 1 953 240 | 5/1971 |
| DE | 29 38 353 | 4/1981 |
| DE | 30 08 848 | 9/1981 |
| DE | 33 28 691 | 2/1985 |
| DE | 36 30 162 | 3/1987 |
| DE | 43 42 042 | 6/1995 |
| DE | 44 20 368 | 12/1995 |
| DE | 196 48 999 | 5/1998 |
| DE | 198 45 512 | 4/2000 |
| DE | 200 03 712 | 8/2000 |
| EP | 0 027 554 | 4/1981 |
| EP | 0 264 065 | 4/1988 |
| EP | 0 276 775 | 8/1988 |
| EP | 1 013 630 | 6/2000 |
| GB | 1 225 210 | 3/1971 |
| GB | 1 384 407 | 2/1975 |
| RU | 2 021 451 | 10/1994 |
| WO | WO-96/35653 | 11/1996 |
| WO | WO-00/29359 | 5/2000 |
| WO | WO-03/093207 | 11/2003 |

OTHER PUBLICATIONS

Wollrum, J., "Darstellung von Vinylchlorid durch laserinduzierete Radikal-Kettenreaktionen", UMSCHAU, Forschung und Entwicklung, Chemische Synthesen mit Laserlicht 16:480:483 (1984).

* cited by examiner

METHOD FOR PRODUCING UNSATURATED HALOGENIC HYDROCARBONS AND DEVICE SUITABLE FOR USE WITH SAID METHOD

RELATED APPLICATIONS

This application is a national stage application (under 35 U.S.C. 371) of PCT/EP03/04519 filed Apr. 30, 2003 which claims benefit to German application Ser. No. 102 19 723.7 filed May 2, 2002.

The present invention relates to a process for preparing unsaturated halogen-containing hydrocarbons from saturated halogen-containing hydrocarbons and also a device which is particularly useful for carrying out the process. A preferred process relates to the preparation of vinyl chloride (hereinafter also referred to as "VC") from 1,2-dichloroethane (hereinafter also referred to as "DCE").

The incomplete thermal dissociation of DCE to produce VC has been carried out industrially for many years. This is carried out using dissociation ovens in which the DCE is partly thermally dissociated into VC and in hydrogen chloride at oven inlet pressures of from 0.8 to 4 MPa and at temperatures of from 450 to 550° C. Typical dissociation conversions are about 55 mol % of the DCE used.

The process requires considerable amounts of energy for the various process steps, e.g. heating of the DCE to the dissociation temperature, the reaction itself and the subsequent purification of the product mixture. A group of measures for improving the economics of the process is directed at energy recovery, as proposed, for example, in EP-B-276, 775, EP-A-264,065 and DE-A-36 30 162.

A further improvement in the economics of the process could also be achieved by seeking a very high conversion in the dissociation reaction. For this purpose, so-called dissociation promoters (hereinafter also referred to as "pyrolysis promoters") have already been added to the feed gas. These dissociation promoters are compounds which disintegrate into free radicals under the conditions prevailing in the reactor and participate in the chain reaction which leads to formation of the desired products. The use of such compounds is known, for example, from U.S. Pat. No. 4,590,318 or DE-A-3,328,691.

Further processes in which dissociation promoters are used in the pyrolysis of DCE are known from WO-A-96/35,653, U.S. Pat. No. 4,584,420, U.S. Pat. No. 3,860,595, DE-A-1,952,770 and DE-A-1,953,240. In all these processes, these dissociation promoters are added to the gas mixture to be dissociated and free radicals are generated therefrom by thermal decomposition. A step of free radical generation preceding the addition of the dissociation promoters is not disclosed in the prior art.

The earlier WO-A-02/94,743, which is not a prior publication, describes a process and a device for carrying out free-radical gas-phase reactions. Here, a gas which comprises free radicals and is produced by thermal decomposition of dissociation promoters in a preceding step outside the reactor is introduced into the reactor.

It is also known from WO-A-00/29,359 that the operating life of the catalyst can be increased by the presence of hydrogen. The hydrogen is in this case mixed into the feed gas.

It has also already been proposed that a feed gas comprising DCE be mixed with a hot particle and/or gas stream or a hot gas stream and the heat transferred from the latter be used for the pyrolysis of EDC. In the process described in U.S. Pat. No. 5,488,190, the pyrolysis of the feed gas in a dissociation oven is replaced by an ultrapyrolysis in which the hot particles or gases transfer their energy very quickly to the feed gas and in which the pyrolysis has to be carried out within less than one quarter of a second. This document also proposes adding dissociation promoters to the hot particles or gases. In this case, all of the heat of reaction for dissociation of the DCE is introduced into the reaction zone by means of the hot medium injected.

Furthermore, it has already been proposed that DCE be dissociated into free radicals by means of laser light and that these be used in free-radical chain reactions, e.g. for the preparation of vinyl chloride. Examples may be found in SPIE, Vol. 458 Applications of Lasers to Industrial Chemistry (1984), pp. 82-88, in Umschau 1984, number 16, pp. 482, and in DE-A-2,938,353, DE-C-3,008,848 and EP-A-27,554. However, this technology has not been employed in industrial production up to the present time. A reason for this may be that the reactors proposed hitherto are not suitable for long-operation.

The present invention provides a process which allows continuous operation of a dissociation oven for a period longer than in conventional processes.

According to the invention and in contrast to known processes, free initiator radicals are generated from dissociation promoters by means of nonthermal or thermal decomposition in one or more physically delineated regions within or outside the reactor but separately from the actual dissociation reaction and these are, in a subsequent step, introduced into the gas stream moving through the reactor. The provision of elevated concentrations of free initiator radicals in physically delineated regions of the reactor interior promotes the subsequent thermal dissociation of the starting material. In addition, the conditions employed in the generation of the free initiator radicals are such that the formation of carbon deposits is minimized.

It is an object of the present invention to provide a pyrolysis process for halogen-containing aliphatic hydrocarbons, by means of which higher conversions than in conventional processes are possible at the same operating temperature or by means of which the operating temperature can be reduced compared to conventional processes at identical conversions.

It has now been found that an increase in the product yield in the continuous pyrolysis can be produced by introduction of small amounts of gases comprising free initiator radicals into the reactor, without large amounts of these gases having to be added.

In one embodiment (hereinafter referred to as "variant I"), the present invention provides a process for preparing ethylenically unsaturated halogen-containing aliphatic hydrocarbons by thermal dissociation of saturated halogen-containing aliphatic hydrocarbons, which comprises the measures:

a) introducing a feed gas stream comprising heated gaseous halogen-containing aliphatic hydrocarbon into a reactor into whose interior at least one feed line for a gas opens, b) introducing a heated gas containing free radicals generated by thermal or nonthermal decomposition of dissociation promoters through the feed line or lines opening into the reactor, with, in the case of generation of the free radicals by thermal decomposition, the heated gas having at least the temperature corresponding to the temperature of the reaction mixture in the reactor prevailing at the point at which the feed line opens and with, in the case of generation of the free radicals by nonthermal decomposition, the heated gas having at least the temperature corresponding to the temperature of the dew point of the reaction mixture at the point at which the feed line opens into the reactor, and c) setting such a pressure and such a temperature in the interior of the reactor that hydrogen halide and ethylenically unsaturated halogen-containing aliphatic hydrocarbon are formed by thermal dissociation of the halogen-containing aliphatic hydrocarbon, with the proviso that, in the case of generation of free radicals by thermal decomposition, this is achieved by heating a gas comprising dissociation promoters diluted with inert gas or by passing a gas comprising dissociation promoters over a heat source whose surface is flushed with inert gas.

In a further embodiment (hereinafter referred to as "variant II"), the invention provides a process for preparing ethylenically unsaturated halogen-containing aliphatic hydrocarbons by thermal dissociation of saturated halogen-containing aliphatic hydrocarbons, which comprises the measures:

a) introducing a feed gas stream comprising heated gaseous halogen-containing aliphatic hydrocarbon into a reactor into whose interior at least one feed line for a heated gas comprising dissociation promoters opens, d) generating free radicals thermally or nonthermally from dissociation promoters by means of a suitable device within a predetermined volume in the interior of the reactor, e) introducing the heated gas comprising dissociation promoters through the feed line into the predetermined volume, with, in the case of generation of the free radicals by thermal decomposition, the heated gas having at least the temperature corresponding to the temperature of the reaction mixture in the reactor prevailing at the point at which the feed line opens and with, in the case of generation of the free radicals by nonthermal decomposition, the heated gas having at least the temperature corresponding to the temperature of the dew point of the reaction mixture at the point at which the feed line opens into the reactor, and c) setting such a pressure and such a temperature in the interior of the reactor that hydrogen halide and ethylenically unsaturated halogen-containing aliphatic hydrocarbon are formed by thermal dissociation of the halogen-containing aliphatic hydrocarbon.

The process of the invention will be described by way of example for the system DCE/VC. It is also suitable for preparing other halogen-containing unsaturated hydrocarbons from halogen-containing saturated hydrocarbons. In all these reactions, the dissociation is a free-radical chain reaction in which, in addition to the desired product, undesirable by-products are formed and lead to carbon deposits in the equipment in long-term operation.

The preparation of vinyl chloride from 1,2-dichloroethane is preferred.

As heated gas for introduction via the feed line(s) into the feed gas stream, it is possible to use any gas which comprises free radicals derived from dissociation promoters.

In variant I of the process of the invention, the formation of free radicals from dissociation promoters occurs in the feed line to the reactor, preferably just before where the feed line opens into the reactor. The feed line can open at the reactor wall or preferably opens into the interior of the reactor in order to avoid reaction of the free radicals generated with the wall. In this variant, the device for generating free radicals is thus located in the feed line or preferably at its end in the reactor and the free radicals formed are fed via the feed line into the reactor.

In variant II of the process of the invention, the gas comprising dissociation promoters is fed via a feed line into a predetermined volume of the interior of the reactor and the dissociation promoters are dissociated into free radicals there by the action of a device for generating free radicals. Here too, the feed line can open at the reactor wall or preferably opens into the interior of the reactor in order to prevent recombinations of the free radicals generated at the reactor wall. In this variant, feed line and device for generating free radicals are thus separate from one another and the free radicals are formed in the interior of the reactor by action of the device for generating free radicals.

In both variants of the process of the invention, it can also be useful to install a further feed line through which heated inert gas can be introduced into the volume of the reactor, into which the free radicals are introduced or in which free radicals are generated from the dissociation promoters in the vicinity of the opening of the feed line for the gas comprising free radicals or dissociation promoters. This inert gas serves to dilute the reactive components and to prevent the formation of carbon deposits.

Examples of dissociation promoters are known per se. These are generally halogen-containing, preferably chlorine-containing, compounds or molecular oxygen. Examples may be found in the abovementioned U.S. Pat. No. 4,590,318 and DE-A-3,328,691. Under the particular conditions of the process of the invention, DCE, for example, is also regarded as a promoter for the pyrolysis reaction since it disintegrates at, for example, the elevated temperatures set for thermal generation of free radicals into free radicals which promote the further course of the pyrolysis reaction. These free radicals can also be generated by nonthermal decomposition of the DCE, e.g. by means of electric discharges or photolytically.

Preferred dissociation promoters are molecular chlorine, nitrosyl chloride, trichloroacetyl chloride, chloral, hexachloroacetone, benzotrichloride, monochloromethane, dichloromethane, trichloromethane, tetrachloromethane or hydrogen chloride.

The gas which is to be introduced and comprises dissociation promoters or free radicals generated therefrom can further comprise inert gas and/or gases which are constituents of the reaction system.

Examples of inert gases are gases which are inert under the reaction conditions prevailing in the reactor, for example nitrogen, noble gases, e.g. argon, or carbon dioxide.

Examples of gases which are constituents of the reaction system are hydrogen chloride and dichloroethane.

Since the introduction of the gas comprising free radicals should not reduce the temperature in the reactor, it is advisable for the temperature of gases comprising nonthermally generated free radicals to be at least as high as the temperature of the gas stream at the point at which the feed line opens into the reactor, while the temperature of gases comprising thermally generated free radicals is usually considerably higher than the temperature of the gas stream at the point at which the feed line opens into the reactor.

When the free radicals are generated by nonthermal decomposition, it is also possible for the heated gas which comprises free radicals or dissociation promoters and is to be introduced into the reactor to have a temperature which is below the temperature of the reaction mixture at the point at which the feed line opens into the reactor. However, it is necessary for the temperature of the heated gas which comprises free radicals or dissociation promoters and is to be introduced into the reactor to have a temperature which is at least equal to the dew point of the reaction mixture at the point at which the feed line opens into the reactor.

The gas to be introduced is preferably heated only shortly before it is introduced or injected into the feed gas stream. Typical temperatures of the gas to be introduced are in the range from 250 to 1500° C., preferably from 300 to 1000° C.

Typical temperatures of the feed gas stream are in the range from 250 to 500° C.

The effect produced by the gas introduced is dependent not only the selected temperature but also on the nature of the gas and on its amount. It is usual to add a total of not more than 10% by weight, preferably not more than 5% by weight, particularly preferably from 0.0005 to 5% by weight, based on the total mass flow in the reactor.

Typically more than 90%, preferably more than 95%, of the heat of reaction required is supplied by heating of the reactor walls, while the heat introduced via the hot gas comprising free radicals in the case of thermal generation of free radicals produces preliminary decomposition of the promoter substance. In the case of nonthermal generation of free radicals, the heat introduced via the hot gas comprising free radicals serves to keep its temperature above the dew point temperature of the reaction mixture at the point of introduction.

It is assumed that the introduction of a heated gas comprising free radicals promotes the free-radical chain reaction in the feed gas, which ultimately leads to an increased concentration of free radicals and an increased conversion in the dissociation reaction.

As feed lines for the heated gas comprising free radicals, it is possible to use all devices known to those skilled in the art for this purpose. Examples are pipes which open into the reactor and have a nozzle at their end which opens into the reactor. Preference is given to feed lines which have a heating device for the heated gas directly before their end which opens into the reactor.

The open end of the feed lines can be at the reactor wall. The feed lines preferably open into the interior of the reactor, in particular into the middle of the gas stream in the reactor, so that the heated gas does not come into contact with the reactor walls to any significant extent.

The generation of the free radicals from dissociation promoters can occur in the feed lines of the reactor. However, it is also possible for a device for generating free radicals to be installed at the end of the feed line for the gas comprising dissociation promoters or for the device for generating free radicals to be installed in the interior of the reactor and produce an increased concentration of free radicals within a predetermined volume and the feed line to the reactor to open into this predetermined volume and allow the introduction of heated gas, e.g. inert gas and/or gas comprising dissociation promoters.

The generation of free radicals from dissociation promoters can be achieved by thermal or nonthermal methods. Examples of nonthermal methods are photolytic dissociation by means of electromagnetic radiation or particle radiation or the generation of nonthermal plasmas by means of electric discharges.

In variant I of the process of the invention, in the case of generation of free radicals by thermal decomposition, a gas diluted with inert gas and comprising dissociation promoters is used or the gas comprising dissociation promoters is passed over a heat source whose surface is flushed with inert gas. These measures contribute significantly to reducing the tendency for carbon deposits to be formed.

In a preferred embodiment, the gas which comprises the radicals, is diluted with inert gas and is to be introduced is heated electrically in the feed line directly before introduction into the reactor.

In a further preferred embodiment, the gas which comprises dissociation promoters, is preferably diluted with inert gas and is to be introduced is passed through a device for generating free radicals, in particular through an electric discharge section at the end of the feed line directly before introduction into the reactor.

A further preferred variant of the process of the invention comprises generation of a thermal plasma from inert gas, cooling of the thermal plasma to the desired temperature by introduction of inert gas so as to produce a gas having a temperature which is sufficiently high to generate free radicals from a dissociation promoter, mixing of this gas with a dissociation promoter and introduction of this mixture comprising free radicals into the reactor.

A further preferred variant of the process of the invention relates to the use of gases which are derived from dissociation promoters and in which free radicals have been generated by means of an electric discharge, preferably a spark, barrier or corona discharge.

A further preferred variant of the process of the invention relates to the use of gases which are derived from dissociation promoters and in which free radicals have been generated by means of a microwave discharge or a high-frequency discharge.

Another preferred variant of the process of the invention relates to the use of gases which are derived from dissociation promoters and in which heat and free radicals have been generated simultaneously by means of a chemical reaction. Examples are the combustion or catalytic reaction of an excess of chlorine with hydrogen in or just before the point at which the feed line opens into the reactor. Thus, it is possible to use a chlorine/hydrogen flame, with chlorine being used in excess and an inert gas preferably being added. Very particular preference is given to the reaction of an excess of chlorine with hydrogen in the presence of inert gas over a catalytically active surface, e.g. over platinum.

Another preferred variant of the process of the invention relates to the use of gases which are derived from dissociation promoters and in which free radicals have been generated by means of a photochemical reaction in the feed line to the reactor or in a predetermined volume in the interior of the reactor. An example is the use of a radiation source suitable for generating free radicals which has been installed in the feed line to the reactor, e.g. an excimer lamp, a mercury vapor lamp, a laser, or injection of electromagnetic radiation suitable for generating free radicals or of particle radiation, e.g. alpha or beta particles, into the feed line to the reactor or into the reactor.

In a further preferred embodiment of the process of the invention, a reactor which has at least one catalytically active metal located on a gas-permeable support in the interior of the reactor is used.

As catalytically active metal, it is possible to use any metal including metal alloys which is stable under the reaction conditions prevailing in the reactor, for example does not melt. It is assumed that metallic surfaces and/or metal halides formed in the dissociation reaction reduce the activation energy of one or more steps of the free-radical chain reaction and thereby accelerate the reaction further.

Preference is given to using a metal or a metal alloy from transition group 8 of the Periodic Table of the Elements, in particular iron, cobalt, nickel, rhodium, ruthenium, palladium or platinum, or alloys of these metals with gold as catalytically active metal.

Very particular preference is given to rhodium, ruthenium, palladium and platinum.

As gas-permeable supports, it is possible to use all supports which are known -to those skilled in the art and can be applied in selective regions of the interior wall of the reactor and/or the interior of the reactor and are provided with feed lines for flushing gas. The support can be a cage which is formed, for example, by a wire mesh or a perforated metal plate and can accommodate a catalyst bed and through which flushing gas can flow, for example through a central inlet by means of a perforated tube.

Furthermore, the gas-permeable support can be a gas-permeable plate which is surrounded by a flat structure, for example a wire gauze, of catalytically active metal.

The gas-permeable support is preferably a porous shaped body. This can consist of the catalytically active metal. It is preferably a porous ceramic which is, in particular, coated with the catalytically active metal; or it is a porous ceramic doped with the catalytically active metal.

The catalytically active metal can have been applied in any form. in or on the gas-permeable support. Such structures are known to those skilled in the art.

For example, the catalytically active metal can be present in a form having a very large surface area:volume ratio. The catalytically active metal is preferably applied as a coating and/or as dopant on or in the gas-permeable support.

To maintain a very long period of operation, it is necessary for the catalytic activity of the metal to be retained for as long as possible and/or to be able to be restored or regenerated during continuing operation of the reactor.

It has been found that this can be achieved by flushing the catalytic surface with a gaseous reducing agent.

As gaseous reducing agent, it is possible to use all reducing agents for carbonization products which are gaseous at the temperatures prevailing in the reactor. Examples are hydrogen or a mixture of hydrogen and inert gas.

The gaseous reducing agent is introduced via the gas-permeable support and is applied through this to the catalytically active metal.

The gaseous reducing agent can be introduced continuously or at predetermined time intervals.

The gaseous reducing agent can be introduced in undiluted form or together with inert gases such as nitrogen and/or noble gases.

The temperature of the gaseous reducing agent introduced via the gas-permeable support is advantageously matched to the temperature prevailing in the interior of the reactor at the position of the gas-permeable support.

Continuous or intermittent injection of hot gases into the reaction mixture enables the conversion in the pyrolysis reaction to be increased and the product yield to be increased; parallel flushing with inert gas and/or reducing agent enables the formation of carbon deposits on the surface of any catalytically active metal present in the interior of the reactor to be efficiently prevented or retarded and, as a result, the period of operation of the dissociation oven to be increased and the conversion in the dissociation reaction to be raised further. Operation of the reactor is not interrupted during the flushing procedure.

Instead of or together with the gaseous reducing agent, dissociation promoters can also be supplied to the catalytically active metal in the reactor via the gas-permeable support. Examples of these have been mentioned above.

It is preferred that at least one feed line for hot gas comprising dissociation promoters opens in the vicinity of the entry of the feed gas stream into the reactor.

In this way, a heated gas comprising free radicals which is formed from dissociation promoters can be introduced into the reactor at this point, so that a high concentration of free radicals is already present when the feed gas is introduced into the reactor, which helps the chain reaction proceed efficiently.

In a preferred variant of the process of the invention, a heated gas comprising free radicals which is formed from dissociation promoters is introduced into the feed gas stream via a plurality of feed lines during passage through the reactor.

The number of feed lines in the first third of the reactor is very particularly preferably greater than that in the second third and/or in the third third.

The process of the invention can be carried out using the pressures and/or temperatures which are customary per se. Useful operating pressures are in the range from 0.8 to 4 MPa (oven inlet); useful operating temperatures are in the range from 450 to 550° C. (oven outlet) and in the range from 250 to 350° C. (oven inlet). The endothermic dissociation reaction requires continual introduction of energy; this is effected during passage of the gas to be dissociated through the reactor.

The process of the invention makes it possible to reduce the customary operating temperatures. This makes more economical operation possible. Instead of a reduction in the operating temperatures, it is possible to obtain an increase in yield.

A further embodiment of the process of the invention relates to the thermal dissociation of the product gas in an adiabatic after-reactor installed downstream of the reactor, which comprises the measures:

f) introducing the product gas stream comprising heated halogen-containing aliphatic hydrocarbon, hydrogen halide and ethylenically unsaturated halogen-containing aliphatic hydrocarbon from the reactor into an adiabatic after-reactor in which the reaction is continued with the aid of the heat supplied by the product gas stream with cooling of the product gas, and in whose interior at least one feed line for a heated gas which comprises free radicals and has been formed from dissociation promoters optionally opens, and g) if appropriate, introducing a heated gas comprising free radicals generated by thermal or nonthermal decomposition of dissociation promoters through the feed line(s) opening into the adiabatic after-reactor or generating free radicals thermally or nonthermally from dissociation promoters by means of a suitable device within a predetermined volume in the interior of the adiabatic after-reactor, with, in the case of generation of the free radicals by thermal decomposition, the temperature of the heated gas being at least the temperature prevailing in the reaction mixture at the point at which the feed line opens into the adiabatic after-reactor and, in the case of generation of the free radicals by nonthermal decomposition, being at least the temperature which corresponds to the dew point of the reaction mixture at the point at which the feed line opens into the adiabatic after-reactor, with the proviso that, in the case of generation of free radicals by thermal decomposition, this is achieved by heating a gas comprising dissociation promoters diluted with inert gas or by passing a gas comprising dissociation promoters over a heat source whose surface is flushed with inert gas.

Here, the process of the invention can comprise only the measures f) and g) in the adiabatic after-reactor without using an upstream reactor into whose interior space at least one feed line for a heated gas opens.

However, the process of the invention with the measures f) and g) in the adiabatic after-reactor is preferably combined with the use of an upstream reactor into whose interior space at least one feed line for a heated gas opens.

The invention further provides a reactor for carrying out the above-defined process, which comprises the elements:
i) feed line for the feed gas stream comprising saturated halogen-containing aliphatic hydrocarbon opening into the reactor,
ii) at least one feed line for a heated gas opening into the interior of the reactor,
iii) source of a dissociation promoter connected to the feed line,
iv) device for generating free radicals from dissociation promoters installed in the feed line,
v) if appropriate, heating device for heating the gas in the feed line,
vi) heating device for heating and/or maintaining the temperature of the gas stream in the reactor, and
vii) outlet line for the product gas stream of the thermal dissociation comprising ethylenically unsaturated halogen-containing aliphatic hydrocarbon leading from the reactor.

In a further preferred embodiment, the invention also provides a reactor for carrying out the above-defined process, which comprises the elements:
i) feed line for the feed gas stream comprising saturated halogen-containing aliphatic hydrocarbon opening into the reactor,
ii) at least one feed line for a heated gas opening into the interior of the reactor,
iii) source of a dissociation promoter connected to the feed line,
viii) device for generating free radicals from dissociation promoters installed at the end of the feed line,
v) if appropriate, heating device for heating the gas in the feed line,
vi) heating device for heating and/or maintaining the temperature of the gas stream in the reactor, and
vii) outlet line for the product gas stream of the thermal dissociation comprising ethylenically unsaturated halogen-containing aliphatic hydrocarbon leading from the reactor.

In a likewise preferred embodiment, the invention provides a reactor for carrying out the above-defined process, which comprises the elements:
i) feed line for the feed gas stream comprising satuarated halogen-containing aliphatic hydrocarbon opening into the reactor,
ix) device which is installed in the interior of the reactor and generates free radicals from dissociation promoters within a predetermined volume in the interior of the reactor,
x) at least one feed line for a heated gas comprising dissociation promoters opening into the predetermined volume in the interior of the reactor,
iii) source of a dissociation promoter connected to the feed line,
v) heating device for heating the gas in the feed line,
vi) heating device for heating and/or maintaining the temperature of the gas stream in the reactor, and
vii) outlet line for the product gas stream of the thermal dissociation comprising ethylenically unsaturated halogen-containing aliphatic hydrocarbon leading from the reactor.

As reactor, it is possible to use all types which are known to those skilled in the art for such reactions. Preference is given to a tube reactor.

An adiabatic after-reactor which preferably comprises the above-defined elements ii), iii) and iv) or ii), iii) and viii) or ix), x), iii) and v) can be located downstream of the reactor of the invention. In the adiabatic after-reactor, the heat of reaction required is supplied by the heat of the product gas stream fed in, which is cooled thereby.

Instead of the reactor of the invention being combined with an adiabatic after-reactor comprising the elements ii), iii) and iv) or ii), iii) and viii) or ix), x), iii) and v), such an adiabatic after-reactor can also be connected to a reactor known per se which does not have the elements ii), iii) and iv) or ii), iii) and viii) or ix), x), iii) and v).

The feed line for the heated gas preferably comprises metal pipes which open at the wall or preferably into the interior of the reactor and have a nozzle at their ends opening into the reactor and preferably have an electric heating device for the heated gas directly before their ends opening into the reactor. In a preferred variant, this heating device consists entirely of ceramic.

A further preferred embodiment of the reactor of the invention comprises a generator for a thermal plasma, for example a high-frequency plasma generator, which is connected to the reactor, via the feed line for the gas comprising free radicals, with the high-frequency plasma generator being connected, if appropriate, to a further feed line for an inert gas and to a further feed line for a dissociation promoter.

The high-frequency plasma generator is preferably installed on the outer wall of the reactor in the vicinity of the opening of the feed line into the reactor.

A further preferred embodiment of the reactor of the invention comprises a device for generating an electric discharge, preferably a spark, barrier or corona discharge, which is connected to the feed line to the reactor. This is likewise preferably installed on the outer wall of the reactor in the vicinity of the opening of the feed line into the reactor.

A further preferred embodiment of the reactor of the invention comprises a device for generating a microwave discharge or a high-frequency discharge which is connected to the feed line to the reactor. This is likewise preferably installed on the outer wall of the reactor in the vicinity of the opening of the feed line into the reactor.

Another preferred embodiment of the reactor of the invention comprises a device in which heat and free radicals are generated simultaneously by means of a chemical reaction and which has at least two feed lines for the reactants and also a burner which opens directly into the reactor.

A further preferred embodiment of the reactor of the invention comprises a radiation source which is located in the feed line to the reactor or whose radiation is introduced into the feed line to the reactor. This is likewise preferably installed on the outer wall of the reactor in the vicinity of the opening of the feed line into the reactor.

In a very particularly preferred embodiment of the reactor of the invention at least one porous ceramic in the form of a stub whose surface is coated with catalytically active metal and/or which is doped with catalytically active metal is present inside the reactor, and the stub is provided with a feed line for a gaseous reducing agent and/or a dissociation promoter for supply to the catalytically active metal.

Further particularly preferred embodiments of the process and reactor of the invention are described below with the aid of FIGS. 1 to 9.

Figure 2:
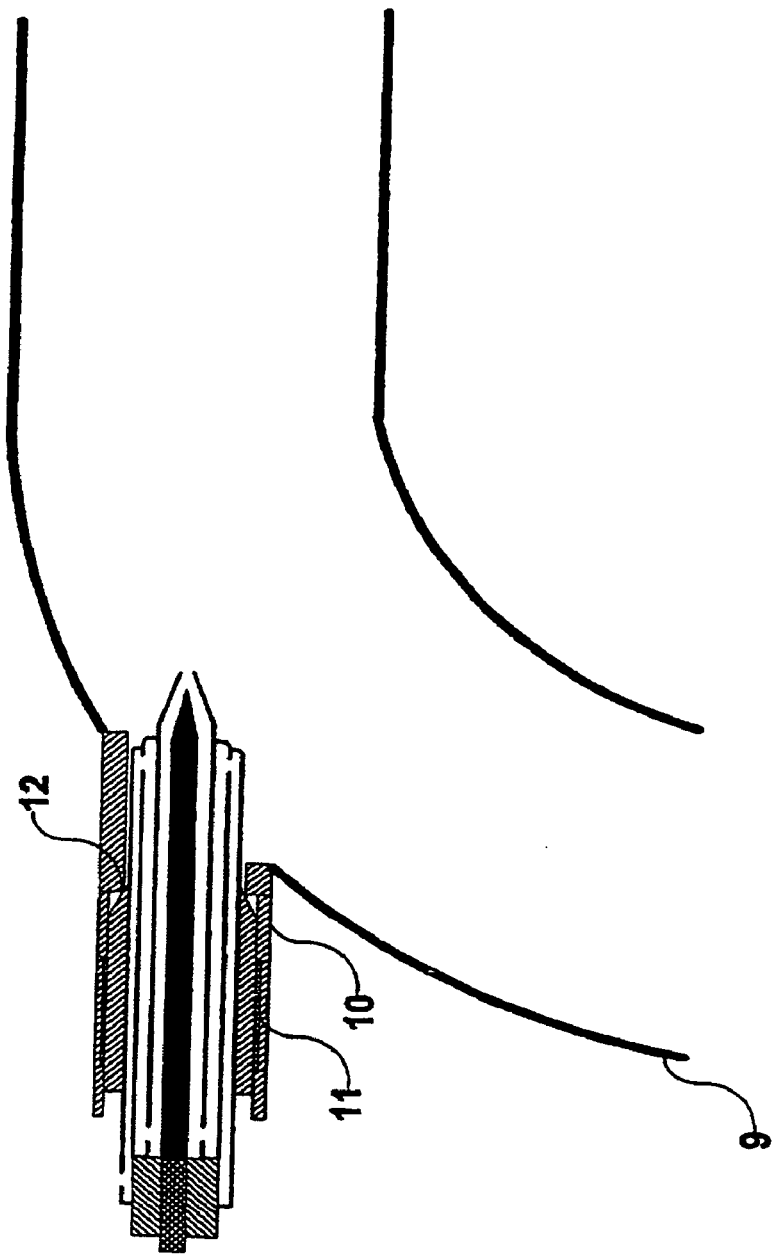
Figure 3:
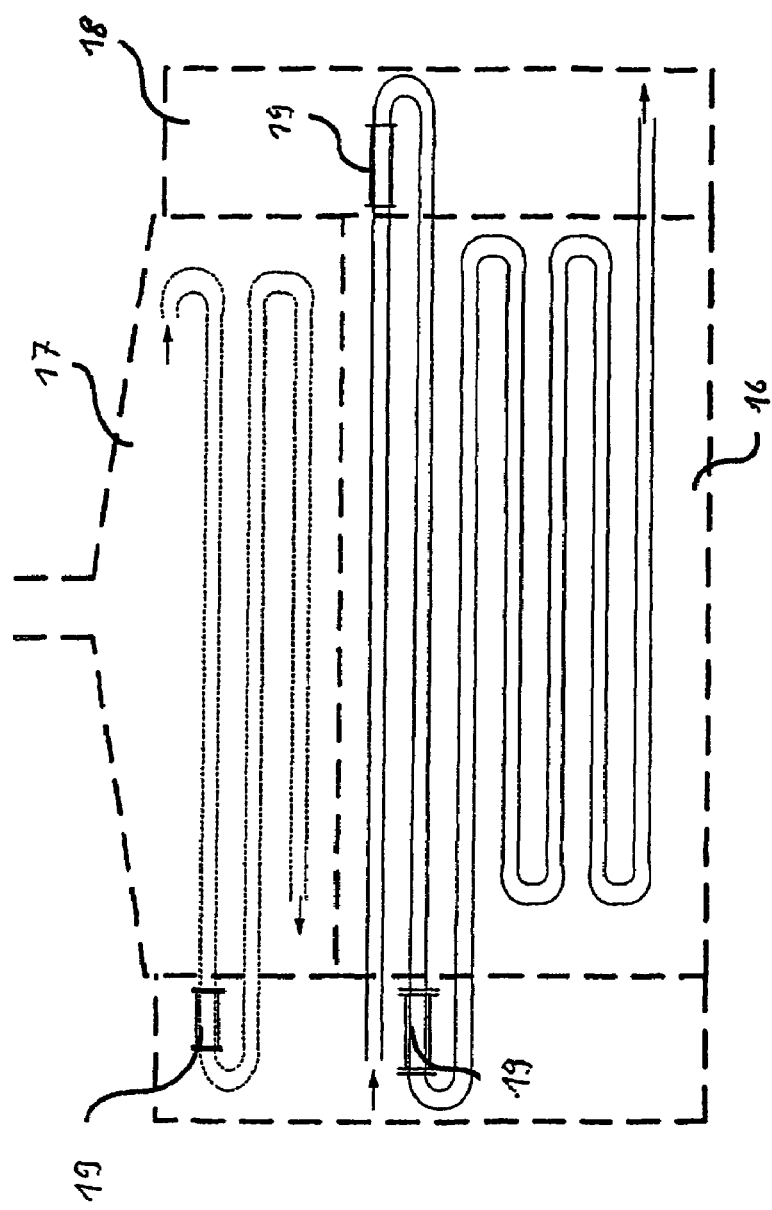
Figure 4:
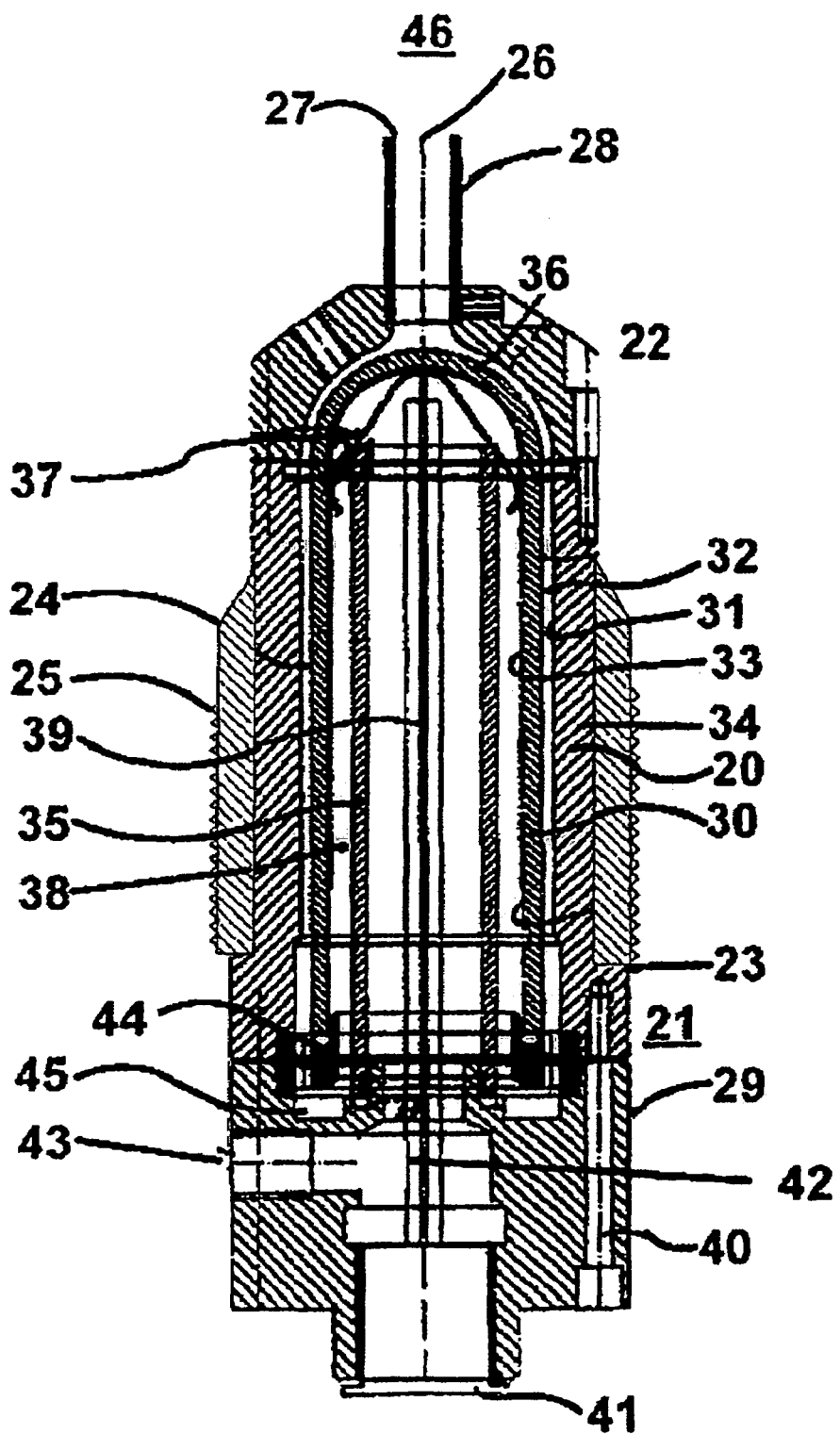
Figure 5:
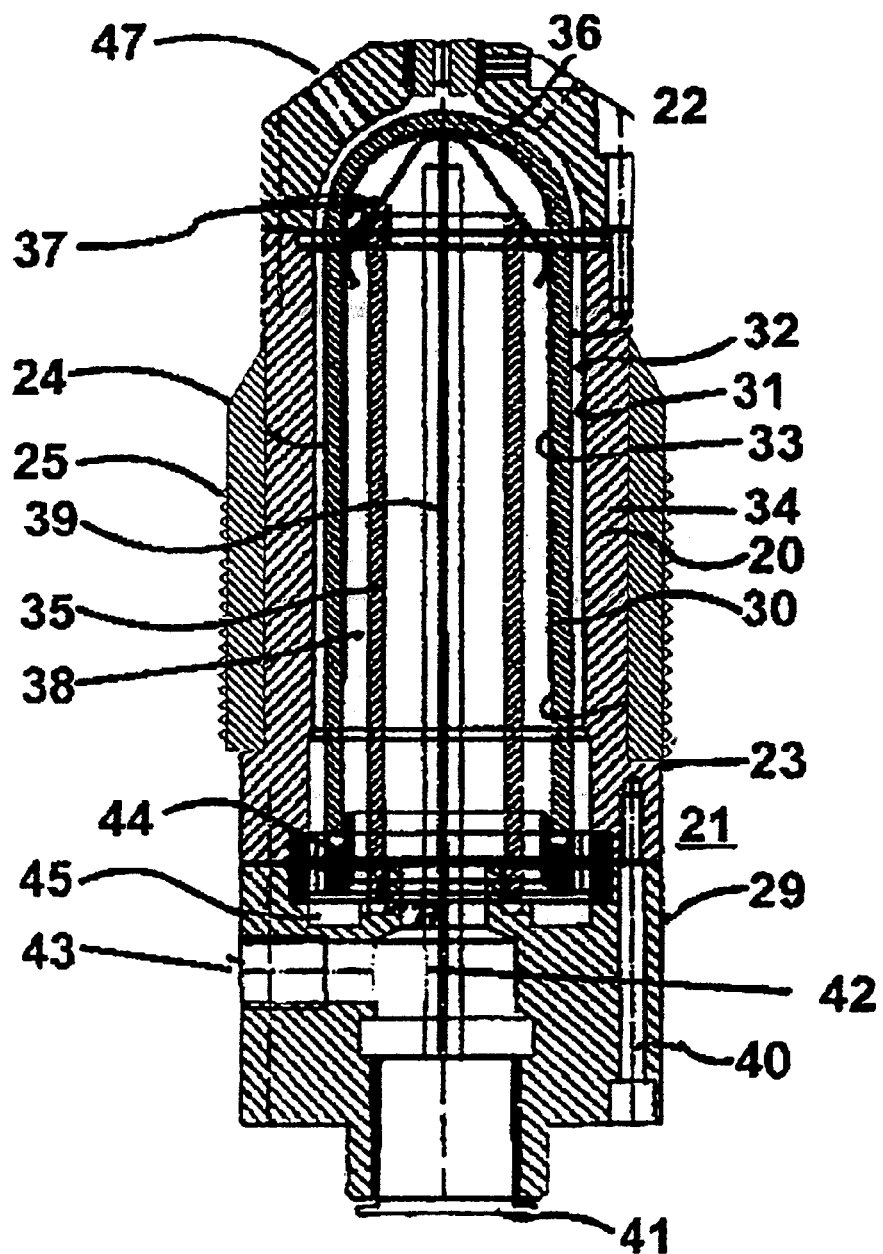
Figure 6:
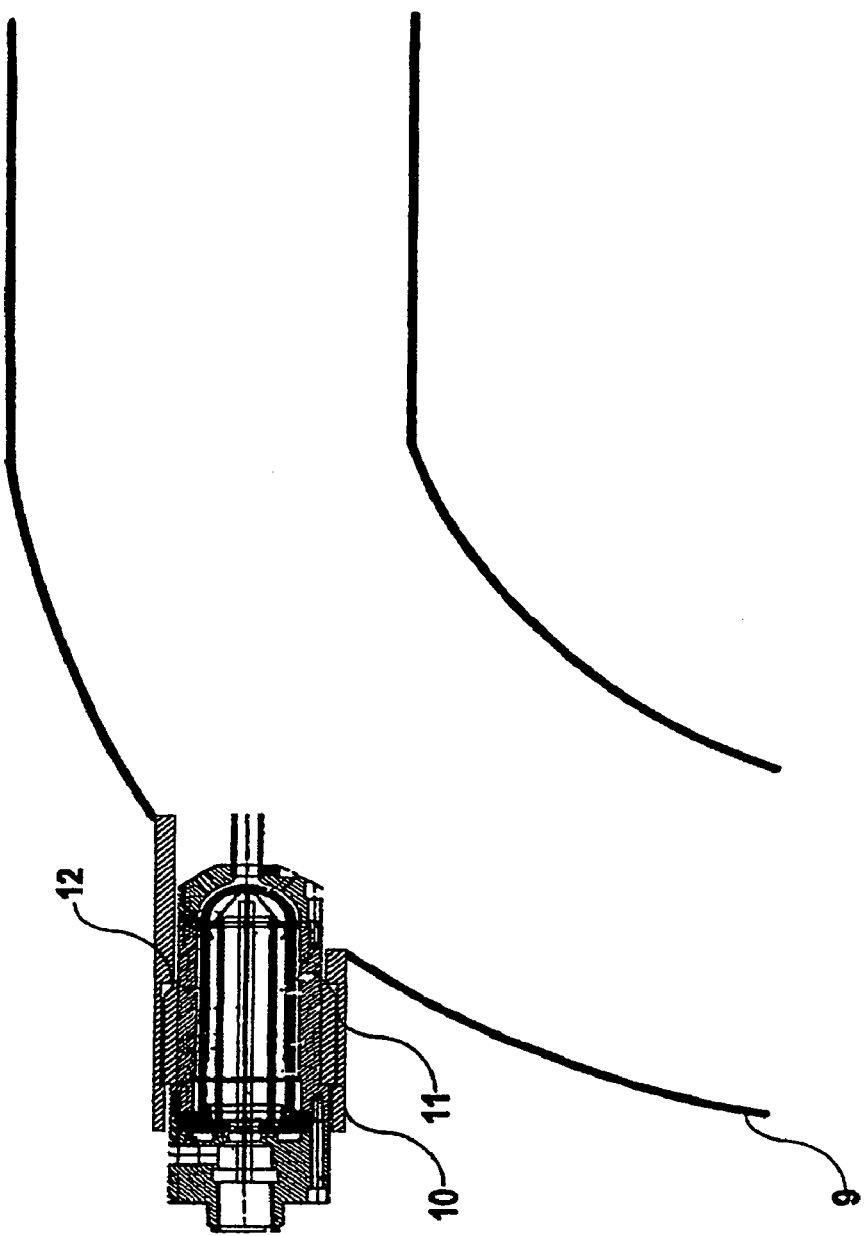
Figure 7:
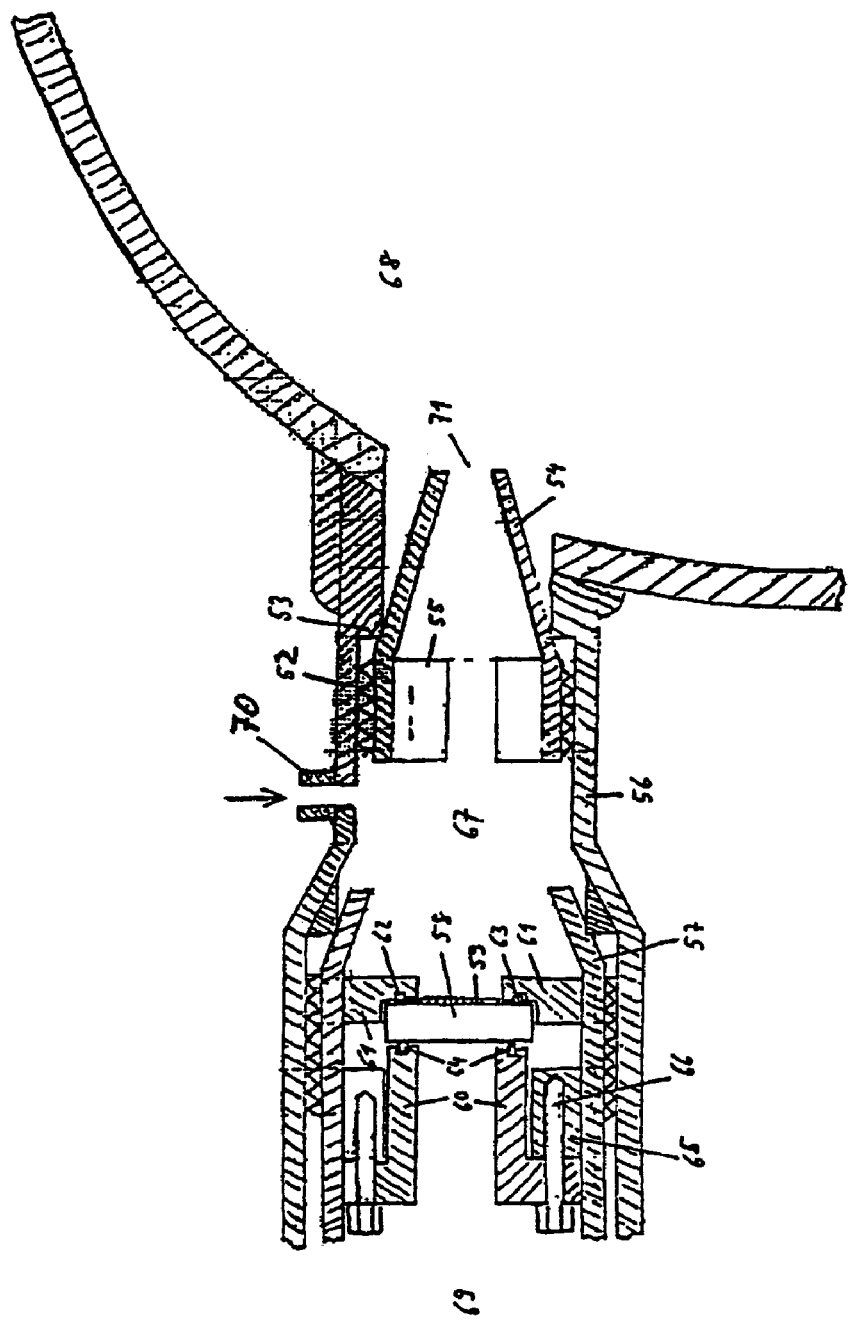
Figure 8:
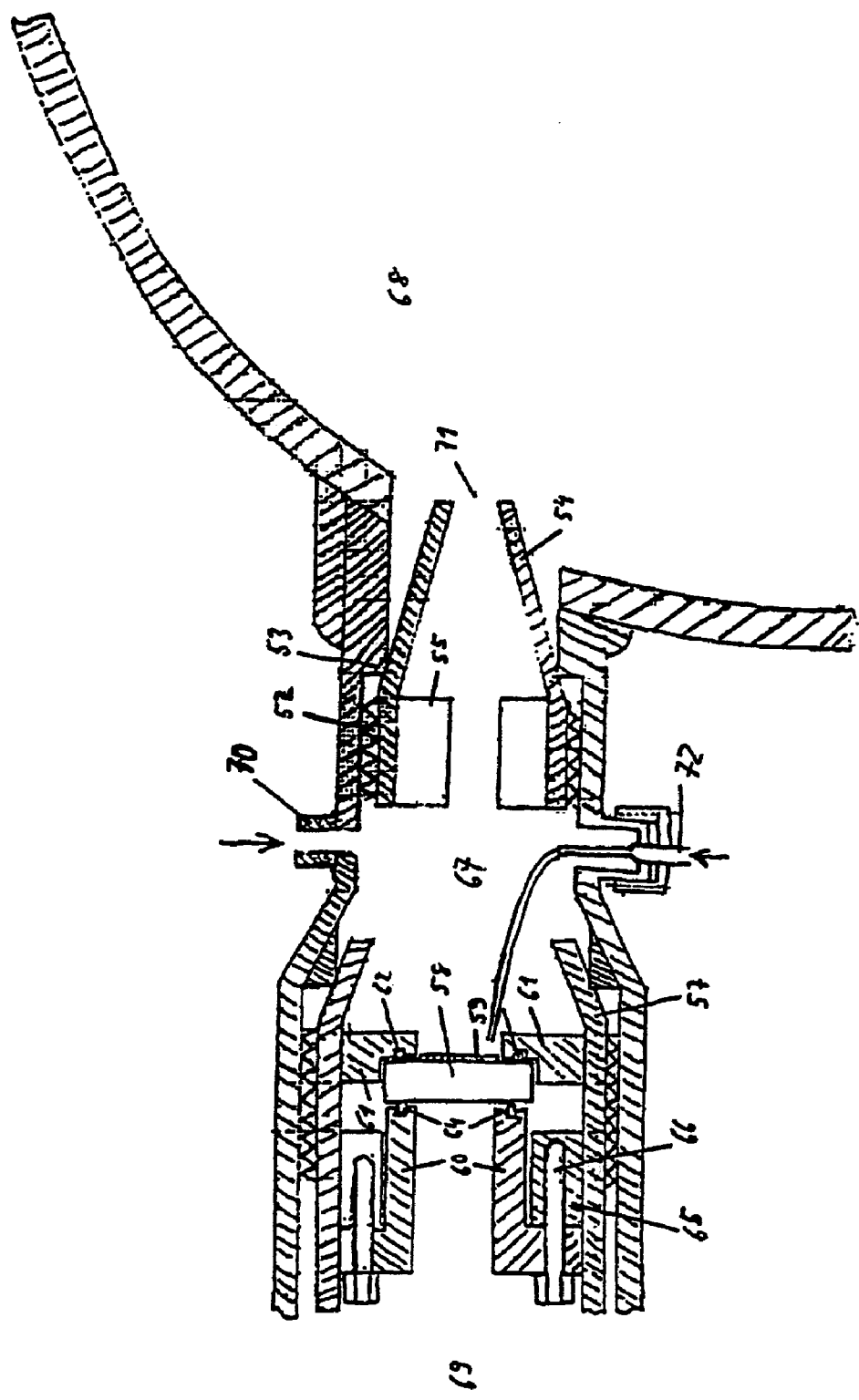
Figure 9:
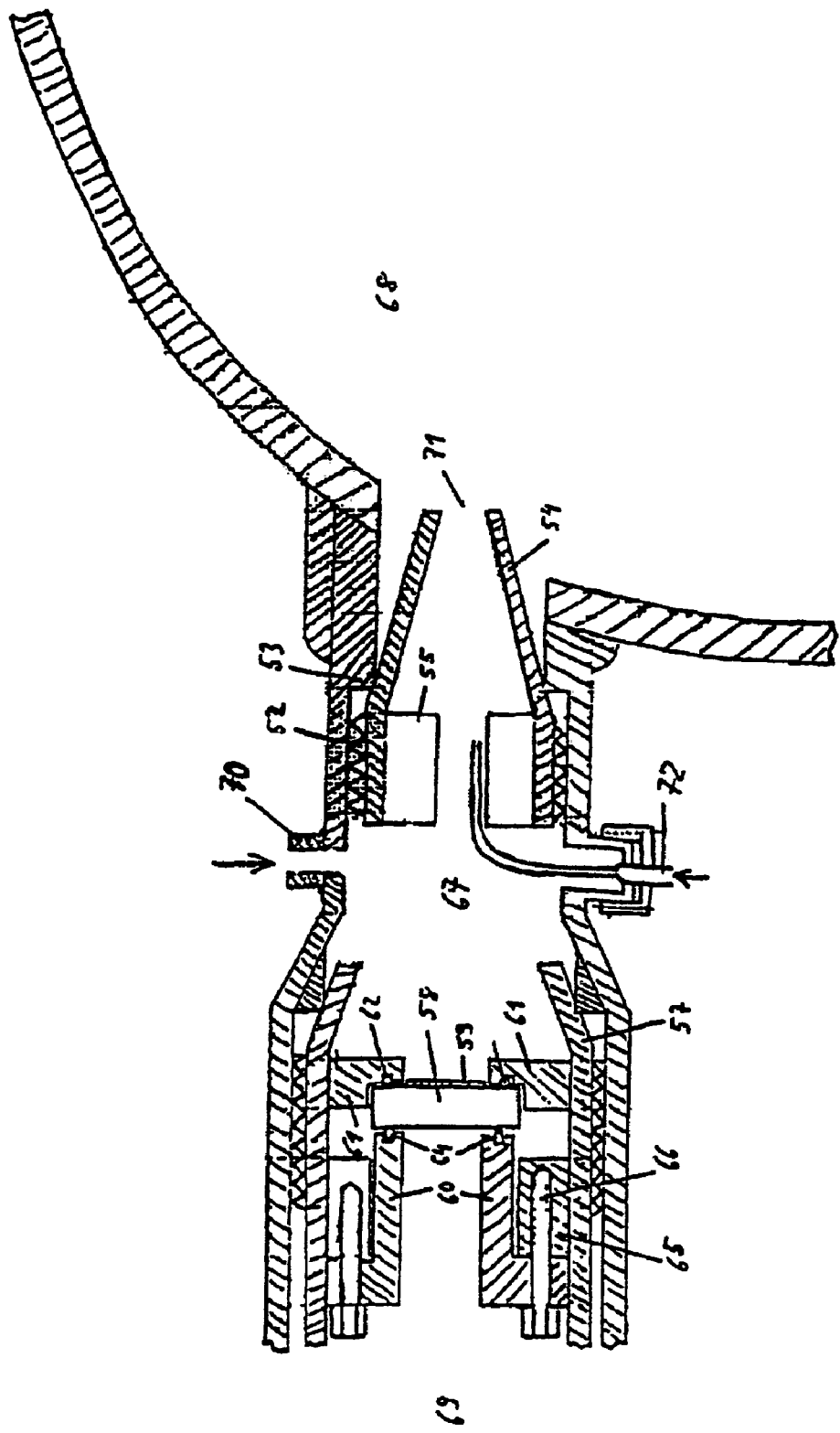

In the figures,

FIG. 1 shows a preferred device for heating and introducing a heated gas which comprises free radicals and has been formed from dissociation promoters into a dissociation reactor shown in longitudinal section, FIG. 2 shows the device of FIG. 1 installed in a reaction tube shown in cross section, FIG. 3 shows a longitudinal section of a tube reactor with a device as shown in FIG. 1, FIG. 4 shows a preferred device for generating free radicals by means of a nonthermal plasma and for introducing the heated gas which comprises free radicals and has been formed from dissociation promoters into a dissociation reactor shown in longitudinal section, FIG. 5 shows a further preferred device for generating free radicals by means of a nonthermal plasma and for introducing the heated gas which comprises free radicals and has been formed from dissociation promoters into a dissociation reactor shown in longitudinal section, FIG. 6 shows the device of FIG. 4 or 5 installed in a reaction tube shown in longitudinal section, FIG. 7 shows a further preferred device for generating free radicals from dissociation promoters by means of radiation and for introducing the gas which comprises free radicals and has been formed from dissociation promoters into a dissociation reactor shown in longitudinal section, FIG. 8 shows a longitudinal section of a modification of the device of FIG. 7, FIG. 9 shows a longitudinal section of a further modification of the device of FIG. 7.

In a particularly preferred variant of the process of the invention, the feed gas stream comes into contact with a gas comprising free radicals which has been generated in one or more heating devices of the type depicted in FIG. 1 during passage through the reactor.

The heating device is an electrically operated heating cartridge (1) which is preferably provided with ceramic cladding and is preferably installed in a housing (2) having one or more concentric annular gaps (3).

The housing (2) comprises ceramic and/or metal. The housing preferably has a cylindrical shape.

The heating cartridge (1) is fixed in the housing (2) by means of a gastight, pressure- and heat-resistant lead-through (4). The lead-through (4) is preferably provided with a screw thread so that the heating cartridge can be screwed and fixed into it.

The housing (2) has a gas inlet (5) through which a gas stream which comprises dissociation promoters and may have been diluted with inert gas can be introduced. The gas inlet (5) is preferably located at the outer wall of the housing (2).

A plurality of concentric annular gaps (3) are preferably formed in the housing, and the gas comprising dissociation promoters flows through these. These annular gaps (3) have at least two openings through which the gas comprising dissociation promoters flows into and out of the annular gap. These openings are preferably located at the height of the front and rear ends of the heating device. As a result, the gas stream flows through each annular gap along the entire length of the heating device and the flow direction of the gas stream is reversed in each annular gap. In the embodiment shown, the gas stream travels from the outside of the housing (2) through the annular gap (3), its flow direction is reversed repeatedly in the annular gaps (3) and the gas stream finally flows along the heating cartridge (1) installed in the middle and then through a gas outlet (6), which is preferably configured as a nozzle, into the reaction space.

However, the housing (2) can also have only one annular gap. In this case, the gas immediately flows along the heating cartridge (1) and through the gas outlet (6) into the reaction space.

The embodiment having a plurality of annular gaps shown in FIG. 1 offers the advantage that the strong heating of the gas comprising dissociation promoters at the heating cartridge (1) does not result in the outer wall of the heating device being heated to a temperature significantly above the temperature prevailing in the reaction space. This prevents increased formation of carbon deposits on the outer wall.

In a further embodiment, the outer wall of the heating device, in particular the part of the heating device which projects into the reaction space, can be coated with an inert material, e.g. a metal oxide, ceramic, boron nitride or silicon nitride.

The interior wall of the heating device opposite the heating cartridge (1) can also be coated with such material.

In a further embodiment, the device has at least two separate gas feed lines, with one feed line serving to introduce an inert gas and the other feed line serving to introduce a promoter substance. The feed line for the promoter substance is preferably arranged so that mixing with the inert gas occurs only just before entry into the reaction space.

The heating device shown in FIG. 1 is provided on its exterior wall with a cone (8) on whose outside there is a thread (7). The cone (8) and that part of the heating device which forms the sealing edge for the seal to the line consist of materials which have approximately the same thermal expansion, in particular of the same material.

A possible arrangement of the heating device on the reaction tube is shown in FIG. 2. A holder (10) which has a thread (11) and a shoulder (12) which forms a circumferential sealing edge is welded onto the reaction tube (9).

When the heating device described in FIG. 1 is screwed into the holder (10), the shoulder (12) cuts into the cone (8) and thus forms a reliable seal.

This sealing principle has been described in DE-A-44 20 368. Likewise as described in 44 20 368, an additional seal can be provided by means of a gland packing (not shown in FIG. 2).

The heating device shown in FIG. 1 can be installed in a conventional tube reactor for preparing ethylenically unsaturated halogen-containing aliphatic hydrocarbons by thermal dissociation of saturated halogen-containing aliphatic hydrocarbons.

Such installation is shown schematically in FIG. 3.

The tube reactor comprises an oven and a reaction tube.

In general, such an oven fired with a primary energy source such as oil or gas is divided into a radiation zone (16) and a convection zone (17).

In the radiation zone (16), the heat required for pyrolysis is transferred to the reaction tube primarily by radiation from the oven walls which have been heated by means of burners.

In the convection zone (17), the energy content of hot flue gases leaving the radiation zone is exploited, so that convective heat transfer occurs. In this way, the starting material for the pyrolysis reaction, e.g. EDC, can be preheated, vaporized or superheated. The generation of steam and/or preheating of combustion air are likewise possible.

In a typical arrangement as shown, for example, in EP-A-264,065, liquid EDC is firstly preheated in the convection zone of the dissociation oven and is then vaporized in a specific vaporizer outside the dissociation oven. The gaseous EDC can again be passed into the convection zone and superheated there, with the pyrolysis reaction being able to commence at this point. After superheating is complete, the EDC enters the radiation zone where the conversion into vinyl chloride and hydrogen chloride takes place.

Due to the high temperatures prevailing in the radiation zone and at the entry into the convection zone, it is advantageous for the device depicted in FIG. 1 not to be positioned directly within these zones since otherwise, for example, setting a defined temperature of the heated gas or gas mixture comprising free radicals which is introduced to promote the dissociation reaction is impossible or possible only with difficulty.

Preference is therefore given to an arrangement as shown schematically in FIG. 3.

Here, the dissociation furnace is extended to include at least two additional, unheated compartments (18) which may be thermally insulated. Loops of the reaction tube are then passed from the actual radiation or convection zone (16, 17) through these compartments (18). The heating device shown in FIG. 1 (19) for introducing a heated gas comprising free radicals is then installed in these loops, preferably at the bends of the loops and opening into the straight lengths of these loops, i.e. built into the reaction tube so that the feed gas stream can be brought into contact with the heated gas comprising free radicals at these points.

The loops of the reaction tube passed from the radiation or convection zone (16, 17) into the unheated compartments (18) are preferably provided with thermal insulation.

In a further, particularly preferred variant of the process of the invention, the feed gas stream comes into contact, during passage through the reactor, with a nonthermal plasma comprising free radicals which has been generated in one or more devices of the type depicted in FIGS. 4 and 5.

FIGS. 4 and 5 show a device known per se for the upstream generation of free radicals by means of a nonthermal plasma derived from a vaporous dissociation promoter or a mixture of dissociation promoter and inert gas and for introduction of the plasma into the reactor of the invention.

Here, free radicals are generated from a gaseous dissociation promoter by means of an electric discharge in a volume separate from the reaction space of the dissociation reaction. It is possible to use the undiluted dissociation promoter, or the promoter can be diluted with an inert gas such as nitrogen or noble gas. The electric discharge is preferably a barrier or corona discharge. The free radicals generated in this way are then fed into the actual reaction space of the reactor of the invention.

The device shown in FIGS. 4 and 5, which is preferably used in the reactor of the invention, is known from DE-A-196 48 999. The previously known device is used for the treatment of surfaces with a high-pressure plasma.

The device for generating a nonthermal plasma is advantageously combined with a sealing system as is known from DE-A-44 20 368 for the introduction of a measuring sensor into a dissociation oven for the production of vinyl chloride.

As a difference from the procedure described in DE-A-196 48 999, the device for plasma generation is operated at significantly higher pressures of at least 5 bar, preferably from 12 to 26 bar, according to the invention.

In contrast to the operation at atmospheric pressure known from DE-A-196 48 999, significantly higher electric potentials are necessary for generating, for example, a barrier discharge.

The device for plasma generation which is preferably used according to the invention comprises a gas inlet (43), a plasma generation region (32) having at least two electrodes (33, 34) and a gas outlet (28) which opens into a reaction space (46), with the reaction space (46) and plasma generation region (32) being physically separate from one another.

An example of the device used in the reactor of the invention and described in DE-A-196 48 999 is described in more detail below with reference to FIG. 4, which shows a longitudinal section.

The device has an essentially cylindrical housing (20) having a rear end (21) and a front end (22). Along its outside (23), the housing (20) is provided with a cone (24) and a thread (25). The housing (20) consists of a conductive material such as metal, preferably steel or another metal, which is stable under the conditions prevailing in the reactor.

In the region of its front end (22), the cylindrical housing (22) tapers and has an opening serving as gas outlet (28) in the region of its cylinder axis (26). This opening can be formed by a port. In the region of its rear end (21), the housing (20) bears a flange (29) which has channels and inlets as described further below.

In the interior of the housing (20), a ceramic tube (30) which is closed at one end in the region of the gas outlet (27) is installed axially symmetrically to the axis (26). The external diameter of this ceramic tube (30) is selected so that an annular gap which will hereinafter be referred to as the plasma generation region (32) is formed between the ceramic tube (30) and the inside (31) of the housing (20). The. inside of the ceramic tube (30) is provided with a conductive coating comprising a metal, for example a conductive silver coating, and forms one electrode (33) of a plasma generation device. The other electrode (34) is formed by the electrically conductive housing (20) itself. The ceramic tube (30) and the plasma generation region (32) in the form of an annular gap are thus present between the electrode (33) configured as an interior coating and the electrode (34) formed by the housing (20).

A further tube (35) is present in the interior of the ceramic tube (30) and is likewise installed axially symmetrically to the cylinder axis (26) but is open at both ends. This further tube (35) is fixed with a spacing in the region of the front end (22) of the housing (20) within the ceramic tube (30) with the aid of a spring (37) which presses against the closed end (36) of the ceramic tube (30), so that an annular gap (38) is formed between the outside of the further tube (35) and the conductively coated inside of the ceramic tube (30). The spring (37) is, for example, three- or four-bladed and in each case allows unhindered passage of gas from the interior space of the further tube (35) into the annular gap (38).

The spring (37) also connects a high-voltage lead (39) located axially symmetrically within the further tube (35) with the electrically conductive coating which forms the one electrode (33), so that an alternating current can be supplied to the latter. On the other hand, the housing (20) forming the other electrode (34) is earthed, so that it can be touched without danger.

The flange (29) at the rear end (21) of the cylindrical housing (20) serves essentially to supply gas and high-voltage power and to earth and conduct the gas flow through the various gaps within the housing (20). The cylindrical flange (29) is fastened to the cylindrical housing (20) by means of screws (40) which are screwed into the outer region of the cylindrical housing (20). In its middle, the flange (29) has an insulating, gastight and pressure-resistant lead-through (41) through which the high-voltage lead (39) is passed axially into the housing (20). Furthermore, the flange (29) has a gas inlet (43) which leads from an outer connecting piece via a channel (42) into the interior region of the further tube (35), and the rear end of the further tube (35) seals against a sealing web (44) of the flange (29).

Furthermore, the flange (29) has on its side facing the housing (20) a circular groove (45) whose diameter is measured such that it connects the annular gap (38) between the further tube (35) and the ceramic tube (30) to the annular gap of the plasma generation region (32) between the ceramic tube (30) and the inside (31) of the housing in a gastight fashion.

To operate the device, the gas inlet (43) is supplied with the chosen gas or gas mixture and a high-frequency high voltage is applied between the high-voltage lead (39) and the housing (20). The voltage and frequency to be selected depend on the type of gas, the geometry of the assembly, the type of surface treatment and further factors and can be chosen freely by a person skilled in the art.

The gas goes from the gas inlet (43) into the interior of the further tube (35), flows through this further tube (35) to the spring (37), enters the region between the spring (37) and the closed end of the ceramic tube (30) and travels back down again into the annular gap (38) between the ceramic tube (30) and the further tube (35). The gas then again reaches the flange (29) in its circular groove (45) and is once again deflected, this time in an upward direction, into the annular gap between the outside of the ceramic tube (30) and the inside of the housing (20), which forms the plasma generation region (32). After flowing through this plasma generation region, the gas reaches the region of the gas outlet (28) and there leaves the device and enters the reaction space (46) where the reaction to be initiated occurs.

Since the conductive coating of the ceramic tube (30) is at the same electric potential as the high-voltage lead (39), the gas remains uninfluenced electrically both within the further tube (35) and in the annular gap (38). The diversion of the gas through the further tube (35) and the annular gap (38) is carried out essentially for the purpose of internal cooling of the device. The working gas thus acts simultaneously as cooling gas, which enables further internal cooling to be dispensed with.

Only in the plasma generation region (32) is the gas present between the electrodes (33), formed by the conductive coating of the ceramic tube (30), and (34), formed by the housing (20), and is partially ionized by the applied high-frequency high voltage, i.e. converted into the plasma state desired for generation of free radicals. In operation of the device, the flow velocity selected should be sufficiently high for the plasma state to be maintained even after exit of the plasma gas through the gas outlet (28).

In a further embodiment, the exterior wall of the device used according to the invention, in particular the part of the device which projects into the reaction space, can be coated with an inert material, e.g. a metal oxide, ceramic, boron nitride or silicon nitride, to retard or prevent the deposition of carbon.

In a further embodiment shown in FIG. 5, the device has one or more drilled holes (47) in the housing (20) in place of the gas outlet (28), so that the gas comprising free radicals can travel out through these holes (47) into the reaction space (46).

The device used according to the invention is preferably provided on its exterior wall with a cone (24) and a thread (25).

A preferred way of installing the devices of FIGS. 4 and 5 on the reaction tube is shown in FIG. 6.

A holder (49) which has a thread (50) and a shoulder (51) which forms a circumferential sealing edge is welded onto the reaction tube (48). When the device described in FIG. 4 or FIG. 5 is screwed into the holder, the sealing edge (51) cuts into the cone (46) and a reliable metallic seal is formed.

This sealing principle is known from DE-A-4,420,368. Likewise as described there, an additional seal can be provided by a gland packing (not shown in the figure).

The entire device can be installed on the reactor in the same way-as shown in FIG. 3.

In a further, particularly preferred variant of the process of the invention, the feed gas stream comes into contact with a gas which comprises free radicals and has been generated in one or more devices of the type depicted in FIGS. 7, 8 and 9 during passage through the reactor.

In this device, free radicals are generated by photolysis of a gaseous promoter substance which can either be in pure form or be present in admixture with an inert gas and/or with a gaseous reducing agent.

Photolysis takes place in a compartment which is separate from the actual reaction space and through which the respective gas (mixture) flows and is dissociated photolytically into free radicals. The gas (mixture) comprising free radicals then goes through an opening, which can be configured as a nozzle, into the actual reaction space.

During flow through the compartment, but optionally also after exit from the nozzle, the promoter substance is photolyzed by interaction with light from a suitable light source. This results in formation of free radicals which then promote the reaction occurring in the actual reaction space. This procedure has the advantage that only small amounts of promoter substance are needed.

The direct introduction of a promoter substance into the reaction space, as is known from the literature, leads to generation of free radials by thermal disintegration of the promoter at the temperature level of the reaction to be influenced, for example in the range 450-550° C., or by heterogeneous disintegration (wall reactions). In this case, the promoter has to be added in amounts which have an appreciable effect on the reaction system and lead not only to the desired increase in conversion but also to increased formation of by-products, i.e. to a reduction in the selectivity, and to an increase in the rate of formation of carbon deposits.

These disadvantages nullify the economic advantage gained by the increasing conversion and lead to the use of promoter substances not having been able to become established in industrial practice to the present day.

The procedure described here overcomes this disadvantage by the promoter substance being decomposed into free radicals specifically and effectively in a compartment separate from the actual reaction, so that it is necessary to add only small amounts of promoter substance.

Promoter substances in the preparation of halogen-containing ethylenically unsaturated hydrocarbons are usually substances which form chlorine radicals under the reaction conditions of the process. These can be chlorine itself or chlorine compounds such as $CCl_4$ or other chlorinated hydrocarbons. In the process described here, the promoter substance can also be DCE, which is then preferably diluted with an inert gas.

To carry out the process variant described, light from a light source suitable for the purpose described is introduced via a light conductor or an optically transparent window, preferably a fused silica window, into a compartment separate from the actual reaction space and passes through the compartment itself and preferably also part of the adjoining reaction space.

In the compartment, the promoter gas (which can consist of the pure promoter substance or be a mixture of promoter substance with an inert gas) forms a gas buffer which largely isolates the light conductor or the optical window chemically from the reaction space. The purpose of this measure will be explained below for the example of EDC dissociation.

An undesirable secondary reaction in EDC dissociation is the deposition of carbon on the reactor walls. The process of carbon deposition proceeds more slowly on nonmetallic materials, e.g. fused silica, than on metallic materials. Good use has in recent times been made of this fact to retard the formation of carbon deposits in reactor tubes by application of nonmetallic coatings to the interior wall of the tube. Despite this fact, carbon would also be deposited on the optical window if this were exposed directly to the reaction mixture, i.e., for example, were to be installed directly in the wall of the reactor.

These problems have been described in DE-A-30 08 848. There, photochemical initiation of the dissociation reaction by direct radiation of light into the reaction space is proposed, both when using metal vapor lamps and when using lasers as light source. The observation that the window is rapidly covered with by-products when continuously operating light sources such as metal vapor lamps are used while it remains free when lasers are used is also described there.

As a remedy, operation using a high flow velocity in the region of the optical window is proposed, so that the by-products formed are formed in an appreciable amount only downstream of the window.

However, this procedure has the disadvantage that the "self-cleaning" of the window is probably restricted to the use of pulsed lasers, since in this case pressure pulses are generated by brief local heating of the gas in and around the carbon particles and these pressure pulses then detach the carbon particles or the carbon layer from the window. Although the use of pulsed lasers is not mentioned explicitly in DE-A-30 08 848, it is mentioned in DE-A-29 38 353 which is expressly incorporated by reference in DE-A-30 08 848.

The experiments on which DE-A-30 08 848 and DE-A-29 38 353 are based were carried out in fused silica reactors. However, in industrial reactors made of metal, carbon deposits would be formed in the inlet region of the reactor and thus "upstream" of any optical window installed. Possible causes for this are, firstly, that precursors of carbon deposits are formed in the inlet region of the reactor by reactions at the wall and, secondly, that small amounts of precursors of carbon deposits can be introduced into the reactor together with the starting material in the industrial process even when the starting DCE is carefully purified by distillation. There is therefore a need for further processes which can readily be implemented in industrial practice and in which formation of carbon deposits can be avoided effectively.

These disadvantages are overcome by means of the present invention and a process and/or a reactor is available in which light can be introduced into a reactor operated under the conditions of VC production or under similar conditions is/are proveded. For this purpose, a promoter substance is firstly photolytically dissociated in a compartment separate from the actual reaction space and then introduced into the reaction space.

FIG. 7 shows a device for the photolytic generation of free radicals from dissociation promoters which is preferably used in the reactor of the invention. A holder which has a thread (52) and a circumferential sealing edge (53) in its interior is welded on at a bend of the reaction tube. A conical shell (54) whose front end can be configured as a nozzle and can have, for example, an internal hexagonal hole (55) to aid screwing on can be screwed into this holder. When the conical shell (54) is screwed into the holder (56), it forms a seal which is reliable under the conditions of the reaction with the sealing edge (53) of the holder. This tried-and-tested sealing principle has been described in DE-A-44 20 368.

Using the same sealing principle, a further shell (57) having an optically transparent window (58), e.g. a fused silica window which can be coated with a semitransparent metal layer (59), can be screwed into the holder (56). The metal is preferably a hydrogenation catalyst and very particularly preferably a platinum metal.

The optical window is clamped between holders (60, 61) which on their sides facing the window have circumferential recesses (62) which can each accommodate a seal (63, 64), preferably a metal seal and very particularly preferably a gold seal.

The window (58) is pressed against the holder (61) by the holder (60). This can be achieved by screwing the holder (60) in by means of a bearing ring or bearing blocks (65) provided with, for example, pocket holes (66).

The holders (60) and (61), the recesses (62) and the thicker of the seals have dimensions such that when the assembly is screwed together, the seals exert a defined pressure and the optical window is not damaged.

The intermediate space (67) between the shells (54) and (57) is provided with one or more gas feed lines and forms a compartment separated from the reaction space (68) and the surrounding space (69).

The pyrolysis of, for example, DCE to form VC takes place in the reaction space (68). The entire assembly is installed at a bend of the reaction tube which projects from the actual radiation zone of the oven and is thermally insulated from this.

An inert gas, e.g. nitrogen or a noble gas, or a mixture of an inert gas with a promoter substance or a gaseous promoter substance flows through the gas inlet (70) into the compartment (67). The gas leaves the compartment and flows through the opening (71) into the reaction space.

As a result of the permanent flushing of the compartment, the optical window is separated by a gas buffer from the reaction space (68). Precursors of carbon deposits, e.g. acetylene, benzene or chloroprene, can therefore not reach the window and form carbon deposits there.

In a preferred embodiment, the optical window is coated with an optically semitransparent metal layer, with the metal being a hydrogenation catalyst, e.g. palladium.

If a small amount of hydrogen is then mixed into the promoter gas, precursors of carbon deposits which despite the flushing reach the optical window are reduced on its surface. As a result, carbon deposits cannot form on the surface of the window.

The light from the light source passes through the optical window and transfers energy to the molecules of the promoter substance which as a result disintegrates into free radicals (photolysis) which then promotes the reaction occurring in the actual reaction space (68). The generation of free radicals and their subsequent transport into the reaction space is normally difficult, since the free radicals rapidly recombine under the prevailing pressure conditions (typically 9-25 bar).

However, in the arrangement according to the invention, radiation passes through the entire compartment and preferably also the reaction space. This results in the desired free radicals also being formed from the promoter substance in the opening (71) and in the zone of the reaction space adjoining this opening and thus being able to participate with certainty in the reaction. There is therefore no need for high flow velocities of the initiator or flushing gas to transport free radicals generated in the compartment quickly into the reaction space.

This also means that initiation can be carried out using very small amounts of promoter gas, as a result of which the reaction system is affected to only a small extent and the formation of undesirable by-products is largely suppressed.

In a further preferred embodiment shown in FIG. 8, the compartment (67) has a further gas inlet (72) which extends to close to the surface of the optical window (58). This makes it possible to flush the window and its immediate surroundings with inert gas or a mixture of inert gas and hydrogen, while the promoter substance or a mixture of promoter substance and inert gas is introduced through the gas inlet (70). Such an arrangement allows the optical window to be protected against carbon deposits even more effectively.

A further preferred embodiment shown in FIG. 9 is similar to the embodiment shown in FIG. 8. However, the further gas inlet (72) is in this case directed in the direction of the opening (71) and is employed for introducing the promoter substance. The gas inlet (70) is employed purely for the introduction of inert gas or flushing gas. In this way, the free radicals are generated from the promoter substance in the vicinity of the reaction space (68) and away from the optical window (58). This provides further protection for the optical window (58) against carbon deposits.

As light source, it is possible to use any light source whose light is suitable for photolyzing the promoter substance used. This can be a UV lamp (e.g. a metal vapor lamp) or a laser. When lasers are used, it is immaterial in the case of the arrangement proposed here whether a pulsed laser or a continuous laser is used. Excimer lamps can also be used as light source.

The radiation used can be introduced in various ways. Thus, for example, the light can be introduced through a bundle of optical fibers (as indicated in FIG. 8). Furthermore, the light source (e.g. when a metal vapor lamp or excimer lamp is used) can be installed directly in the shell (57) behind the optical window. In this case, appropriate cooling is preferably provided. The light can also be introduced into the shell (57) through a further window and deflected by means of a mirror onto the window (58).

In a particular embodiment, a device similar to that described in DE-A-198 45 512 or DE-Gbm-200 03 712 is used for the introduction of light. The previously known devices are employed for observing processes in the combustion chamber of internal combustion engines during operation and are, for example, used in the form of spark plug adaptors. In addition to their actual intended use, viz. the visual observation of combustion processes, such devices are, owing to their pressure- and heat-resistance, likewise suitable for introducing light into chemical reactors in which the pressure and temperature conditions are similar to those in running internal combustion engines.

If such devices are used, the optical window shown in FIGS. 7, 8 and 9 together with the sealing system described could be omitted. The light guide would then be screwed in the form of an adaptor analogous to one or more spark plug adaptors into a dividing wall located in the shell (55).

The installation of the device for the photolytic generation of free radicals from dissociation promoters on the reactor according to the invention can be effected in the same way as shown in FIG. 3.

The invention claimed is:

1. A reactor which comprises the elements:
   i) a feed line for the feed gas stream comprising saturated halogen-containing aliphatic hydrocarbon opening into the reactor,
   ii) at least one feed line for a heated gas opening into the interior of the reactor,
   iii) a source of a dissociation promoter connected to the heated gas feed line,
   iv) a device for nonthermally generating free radicals from dissociation promoters installed in the feed line for the heated gas,
   v) optionally, a heating device for heating the gas in the feed line,
   vi) a heating device for heating and/or maintaining the temperature of the gas stream in the reactor, and
   vii) an outlet line for the product gas stream of the thermal dissociation comprising ethylenically unsaturated halogen-containing aliphatic hydrocarbon leading from the reactor.

2. A reactor which comprises the elements:
   i) a feed line for the feed gas stream comprising saturated halogen-containing aliphatic hydrocarbon opening into the reactor,
   ii) at least one feed line for a heated gas opening into the interior of the reactor,
   iii) a source of a dissociation promoter connected to the heated gas feed line,
   viii) device for generating free radicals from dissociation promoters installed at the reactor end of the feed line for the heated gas,
   iv) optionally, a heating device for heating the gas in the feed line,
   vi) a heating device for heating and/or maintaining the temperature of the gas stream in the reactor, and
   vii) an outlet line for the product gas stream of the thermal dissociation comprising ethylenically unsaturated halogen-containing aliphatic hydrocarbon leading from the reactor.

3. A reactor which comprises the elements:
   i) a feed line for the feed gas stream comprising saturated halogen-containing aliphatic hydrocarbon opening into the reactor,
   ix) a device which is installed in the interior of the reactor and generates free radicals from dissociation promoters within a predetermined volume in the interior of the reactor,
   x) at least one feed line for a heated gas comprising dissociation promoters opening into the predetermined volume in the interior of the reactor,
   iii) a source of a dissociation promoter connected to the heated gas feed line,
   v) a heating device for heating the gas in the feed line,
   vi) a heating device for heating and/or maintaining the temperature of the gas stream in the reactor, and
   vii) an outlet line for the product gas stream of the thermal dissociation comprising ethylenically unsaturated halogen-containing aliphatic hydrocarbon leading from the reactor.

4. The reactor as claimed in claim 1, characterized in that the reactor is a tube reactor.

5. The reactor as claimed in claim 2, characterized in that the reactor is a tube reactor.

6. The reactor as claimed in claim 3, characterized in that the reactor is a tube reactor.

7. The reactor as claimed in claim 1, which further comprises a generator for a thermal plasma which is connected to the feed line to the reactor, with the feed line being connected to a further feed line for an inert gas and to a further feed line for a dissociation promoter.

8. The reactor as claimed in claim 2, which further comprises a generator for a thermal plasma which is connected to the feed line to the reactor, with the feed line being connected to a further feed line for an inert gas and to a further feed line for a dissociation promoter.

9. The reactor as claimed in claim 3, which further comprises a generator for a thermal plasma which is connected to the feed line to the reactor, with the feed line being connected to a further feed line for an inert gas and to a further feed line for a dissociation promoter.

10. The reactor as claimed in claim 1, which further comprises a device for generating an electric discharge which is connected to the feed line to the reactor.

11. The reactor as claimed in claim 2, which further comprises a device for generating an electric discharge which is connected to the feed line to the reactor.

12. The reactor as claimed in claim 3, which further comprises a device for generating an electric discharge which is connected to the feed line to the reactor.

13. The reactor as claimed in claim 10, wherein the electric discharge is a spark, barrier or corona discharge.

14. The reactor as claimed in claim 11, wherein the electric discharge is a spark, barrier or corona discharge.

15. The reactor as claimed in claim 12, wherein the electric discharge is a spark, barrier or corona discharge.

16. The reactor as claimed in claim 1, which further comprises a device for generating a microwave discharge or a high-frequency discharge, which is connected to the feed line to the reactor.

17. The reactor as claimed in claim 2, which further comprises a device for generating a microwave discharge or a high-frequency discharge, which is connected to the feed line to the reactor.

18. The reactor as claimed in claim 3, which further comprises a device for generating a microwave discharge or a high-frequency discharge, which is connected to the feed line to the reactor.

19. The reactor as claimed claim 1, which further comprises a radiation source which is located in the feed line to the reactor or whose radiation is introduced into the feed line to the reactor.

20. The reactor as claimed claim 2, which further comprises a radiation source which is located in the feed line to the reactor or whose radiation is introduced into the feed line to the reactor.

21. The reactor as claimed claim 3, which further comprises a radiation source which is located in the feed line to the reactor or whose radiation is introduced into the feed line to the reactor.

22. The reactor as claimed claim 2, wherein the device viii) provided is at least one device for generating and introducing a nonthermal plasma comprising free radicals which comprises a gas inlet, a plasma generation region having at least two electrodes and a gas outlet which opens into a reaction space, with the reaction space and plasma generation region being physically separate from one another.

23. The reactor as claimed claim 3, wherein the device ix) provided is at least one device for generating and introducing a nonthermal plasma comprising free radicals which comprises a gas inlet, a plasma generation region having at least two electrodes and a gas outlet which opens into a reaction space, with the reaction space and plasma generation region being physically separate from one another.

24. The reactor as claimed in claim 22, wherein the device viii) has an essentially cylindrical housing having a rear end and a front end, and in that the housing is provided along at least part of its outside with a cone and a thread made of a conductive material which is stable under the conditions prevailing in the reactor.

25. The reactor as claimed in claim 22, which further comprises a reaction tube onto which a holder having a thread and a shoulder is welded and the device viii) is screwed into this holder.

26. The reactor as claimed in claim 23, which further comprises a reaction tube onto which a holder having a thread and a shoulder is welded and the device ix) is screwed into this holder.

27. The reactor as claimed in claim 22, which further comprises an oven and a reaction tube running in a looping fashion in the oven, with the oven having a radiation zone, a convection zone and at least two unheated compartments from or into which loops of the reaction tube are passed from or into the radiation or convection zone, with at least one device viii) being located in at least one compartment, and in which the reaction tube is installed so that the feed gas stream can be brought into contact at these points with a heated gas comprising free radicals.

28. The reactor as claimed in claim 23, which further comprises an oven and a reaction tube running in a looping fashion in the oven, with the oven having a radiation zone, a convection zone and at least two unheated compartments from or into which loops of the reaction tube are passed from or into the radiation or convection zone, with at least one device ix) being located in at least one compartment, and in which the reaction tube is installed so that the feed gas stream can be brought into contact at these points with a heated gas comprising free radicals.

29. The reactor as claimed in claim 1, characterized in that an adiabatic after-reactor which comprises at least one device viii) is located downstream of it and wherein said device viii) is a device for generating free radicals from dissociation promoters installed at the reactor end of the feed line.

30. The reactor as claimed in claim 2, characterized in that an adiabatic after-reactor which comprises at least one device ix) is located downstream of it and wherein said device ix) is a device which is installed in the interior of the reactor and generates free radicals from dissociation promoters within a predetermined volume in the interior of the reactor.

31. The reactor as claimed in claim 3, characterized in that an adiabatic after-reactor which comprises at least one device ix) is located downstream of it.

32. The reactor as claimed in claim 3, characterized in that an adiabatic after-reactor which comprises at least one device viii) is located downstream of it and wherein said device viii) is a device for generating free radicals from dissociation promoters installed at the reactor end of the feed line.

33. The reactor as claimed in claim 2, characterized in that the device viii) provided is at least one device for generating and introducing a gas comprising free radicals which comprises a compartment which is separated from the actual reaction space but is connected to this via at least one opening and has devices for introducing a gas comprising dissociation promoters, and devices for irradiating this gas, so that free radicals are generated photolytically in the compartment and travel through the opening or openings into the reaction space.

34. The reactor as claimed in claim 3, characterized in that the device ix) provided is at least one device for generating and introducing a gas comprising free radicals which comprises a compartment which is separated from the actual reaction space but is connected to this via at least one opening and has devices for introducing a gas comprising dissociation promoters, and devices for irradiating this gas, so that free radicals are generated photolytically in the compartment and travel through the opening or openings into the reaction space.

35. The reactor as claimed in claim 33, characterized in that the device viii) or device ix) wherein has an optical window and/or another light guide into the compartment and said device ix) is a device which is installed in the interior of the reactor and generates free radicals from dissociation promoters within a predetermined volume in the interior of the reactor.

36. The reactor device as claimed in claim 35, characterized in that the optical window and/or the transparent end of the other light guide is coated with an optically semitransparent layer which comprises a metal which is suitable as hydrogenation catalyst.

37. The reactor as claimed in claim 33, characterized in that the device viii) or ix) forms two conical shells which are installed so that an intermediate space which is provided with at least one gas feed line is formed between the shells and, in that a compartment separated from the reaction space and from the exterior space is formed and in that the shell located farthest from the reactor contains an optically transparent window and/or another light guide and wherein said device ix) is a device which is installed in the interior of the reactor and generates free radicals from dissociation promoters within a predetermined volume in the interior of the reactor.

38. The reactor as claimed in claim 33, characterized in that irradiation devices which make it possible for the entire compartment and the adjacent reaction space to be irradiated are provided.

39. The reactor as claimed in claim 7, characterized in that the intermediate space has a further gas inlet which extends into the compartment to near the surface of the optical window and/or the other light guide and makes it possible for the optical window and/or the other light guide and its surroundings to be flushed with inert gas or with inert gas and hydrogen.

40. The reactor as claimed in claim 33, which further comprises a reaction tube onto which a holder having a thread and a shoulder is welded and the device viii) or ix) is screwed into this holder and wherein said device ix) is a device which is installed in the interior of the reactor and generates free radicals from dissociation promoters within a predetermined volume in the interior of the reactor.

41. The reactor as claimed in claim 33, which further comprises an oven and a reaction tube running in a looping fashion in the oven, with the oven having a radiation zone, a convection zone and at least one unheated compartment from or into which loops of the reaction tube are passed from or into the radiation or convection zone, with at least one device viii) or ix) being located in at least one compartment, and in which the reaction tube is installed so that the feed gas stream can be brought into contact at these points with a heated gas comprising free radicals and wherein said device ix) is a device which is installed in the interior of the reactor and generates free radicals from dissociation promoters within a predetermined volume in the interior of the reactor.

42. The reactor as claimed in claim 1, characterized in that an adiabatic after-reactor which comprises at least one device viii) or ix) is located downstream of it and wherein said device viii) is a device for generating free radicals from dissociation promoters installed at the reactor end of the feed line and said device ix) is a device which is installed in the interior of the reactor and generates free radicals from dissociation promoters within a predetermined volume in the interior of the reactor.

43. The reactor as claimed in claim 2, characterized in that an adiabatic after-reactor which comprises at least one device viii) or ix) is located downstream of it and wherein said device ix) is a device which is installed in the interior of the reactor and generates free radicals from dissociation promoters within a predetermined volume in the interior of the reactor.

44. The reactor as claimed in claim 3, characterized in that an adiabatic after-reactor which comprises at least one device viii) or ix) is located downstream of it and wherein said device viii) is a device for generating free radicals from dissociation promoters installed at the reactor end of the feed line.

45. A reactor for carrying out a process for preparing ethylenically unsaturated halogen-containing aliphatic hydrocarbons by thermal dissociation of saturated halogen-containing aliphatic hydrocarbons, which process comprises the steps of:
  a) introducing a feed gas stream comprising heated gaseous halogen-containing aliphatic hydrocarbon into the reactor into whose interior at least one feed line for a gas opens,
  b) introducing a heated gas containing free radicals generated by thermal or nonthermal decomposition of dissociation promoters through the feed line or lines opening into the reactor, with, in the case of generation of the free radicals by thermal decomposition, the heated gas having at least the temperature corresponding to the temperature of the reaction mixture in the reactor prevailing at the point at which the feed line opens and with, in the case of generation of the free radicals by nonthermal decomposition, the heated gas having at least the temperature corresponding to the temperature of the dew point of the reaction mixture at the point at which the feed line opens into the reactor, and
  c) setting such a pressure and such a temperature in the interior of the reactor that hydrogen halide and ethylenically unsaturated halogen-containing aliphatic hydrocarbon are formed by thermal dissociation of the halogen-containing aliphatic hydrocarbon, with the proviso that, in the case of generation of free radicals by thermal decomposition, this is achieved by heating a gas comprising dissociation promoters diluted with inert gas or by passing a gas comprising dissociation promoters over a heat source whose surface is flushed with inert gas and the reactor comprises following the elements:
    i) a feed line for the feed gas stream comprising saturated halogen-containing aliphatic hydrocarbon opening into the reactor,
    ii) at least one feed line for a heated gas opening into the interior of the reactor,
    iii) a source of a dissociation promoter connected to the heated gas feed line, iv) a device for nonthermally generating free radicals from dissociation promoters installed in the feed line for the heated gas, v) optionally, a heating device for heating the gas in the feed line, vi) a heating device for heating and/or maintaining the temperature of the gas stream in the reactor, and vii) an outlet line for the product gas stream of the thermal dissociation comprising ethylenically unsaturated halogen-containing aliphatic hydrocarbon leading from the reactor.

46. A reactor for carrying out a process for preparing ethylenically unsaturated halogen-containing aliphatic hydrocarbons by thermal dissociation of saturated halogen-containing aliphatic hydrocarbons, which process comprises the steps of:

a) introducing a feed gas stream comprising heated gaseous halogen-containing aliphatic hydrocarbon into the reactor into whose interior at least one feed line for a heated gas comprising dissociation promoters opens, d) generating free radicals thermally or nonthermally from dissociation promoters by means of a suitable device within a predetermined volume in the interior of the reactor, e) introducing the heated gas comprising dissociation promoters through the feed line into the predetermined volume, with, in the case of generation of the free radicals by thermal decomposition, the heated gas having at least the temperature corresponding to the temperature of the reaction mixture in the reactor prevailing at the point at which the feed line opens and with, in the case of generation of the free radicals by nonthermal decomposition, the heated gas having at least the temperature corresponding to the temperature of the dew point of the reaction mixture at the point at which the feed line opens into the reactor, and c) setting such a pressure and such a temperature in the interior of the reactor that hydrogen halide and ethylenically unsaturated halogen-containing aliphatic hydrocarbon are formed by thermal dissociation of the halogen-containing aliphatic hydrocarbon and the reactor comprises following the elements:

i) a feed line for the feed gas stream comprising saturated halogen-containing aliphatic hydrocarbon opening into the reactor, ii) at least one feed line for a heated gas opening into the interior of the reactor, iii) a source of a dissociation promoter connected to the heated gas feed line, viii) device for generating free radicals from dissociation promoters installed at the reactor end of the feed line for the heated gas, iv) optionally, a heating device for heating the gas in the feed line, vi) a heating device for heating and/or maintaining the temperature of the gas stream in the reactor, and vii) an outlet line for the product gas stream of the thermal dissociation comprising ethylenically unsaturated halogen-containing aliphatic hydrocarbon leading from the reactor.

* * * * *